United States Patent [19]

Champain et al.

[11] Patent Number: 5,443,061

[45] Date of Patent: Aug. 22, 1995

[54] APPARATUS FOR PROVIDING A BREATHING GAS WITH AN OVERPRESSURE AND PROCESS OF CONTROLLING SUCH APPARATUS INSTALLATION

[75] Inventors: Roger Champain, Les Loges en Josas; Nourredine Kissi, Masny; Daniel Zalkin, Rambouillet, all of France

[73] Assignee: Taema, Antony Cedex, France

[21] Appl. No.: 855,712

[22] Filed: Mar. 20, 1992
(Under 37 CFR 1.47)

[30] Foreign Application Priority Data

Mar. 21, 1991 [FR] France .................. 91 03431

[51] Int. Cl.6 .................. D06F 58/02; A61M 16/00; A62B 7/00; F16V 31/02
[52] U.S. Cl. .................. 128/204.21; 128/204.18; 128/204.23
[58] Field of Search .................. 128/204.21, 204.23, 128/204.26, 204.18; 318/650, 71, 433, 501

[56] References Cited

U.S. PATENT DOCUMENTS

| | | | |
|---|---|---|---|
| 3,886,419 | 5/1975 | Omura et al. | 318/132 |
| 4,169,990 | 10/1979 | Lerdman | 318/138 |
| 4,561,261 | 12/1985 | Kornrumpf et al. | 62/126 |
| 4,621,503 | 11/1986 | Woods et al. | 62/228.3 |
| 4,825,330 | 4/1989 | Walchle | 361/95 |
| 4,905,687 | 3/1990 | Ponkala | 128/204.21 |
| 5,117,819 | 6/1992 | Servidio et al. | 128/204.18 |
| 5,134,995 | 8/1992 | Gruenke et al. | 128/207.18 |
| 5,166,592 | 11/1992 | Bashark | 318/799 |

FOREIGN PATENT DOCUMENTS

| | | | |
|---|---|---|---|
| WO88/10108 | 12/1988 | WIPO | 128/204.23 |
| WO89/10768 | 11/1989 | WIPO . | |
| WO90/14121 | 11/1990 | WIPO | 128/204.23 |

*Primary Examiner*—Kimberly L. Asher
*Attorney, Agent, or Firm*—William S. Frommer

[57] ABSTRACT

The turbine which generates overpressure for a breathing gas is controlled by detecting recurring variations in the operation of the turbine and correspondingly modifying the control signal which is set to a level which determines the overpressure of the turbine, thereby modulating the overpressure supplied by the turbine.

9 Claims, 1 Drawing Sheet

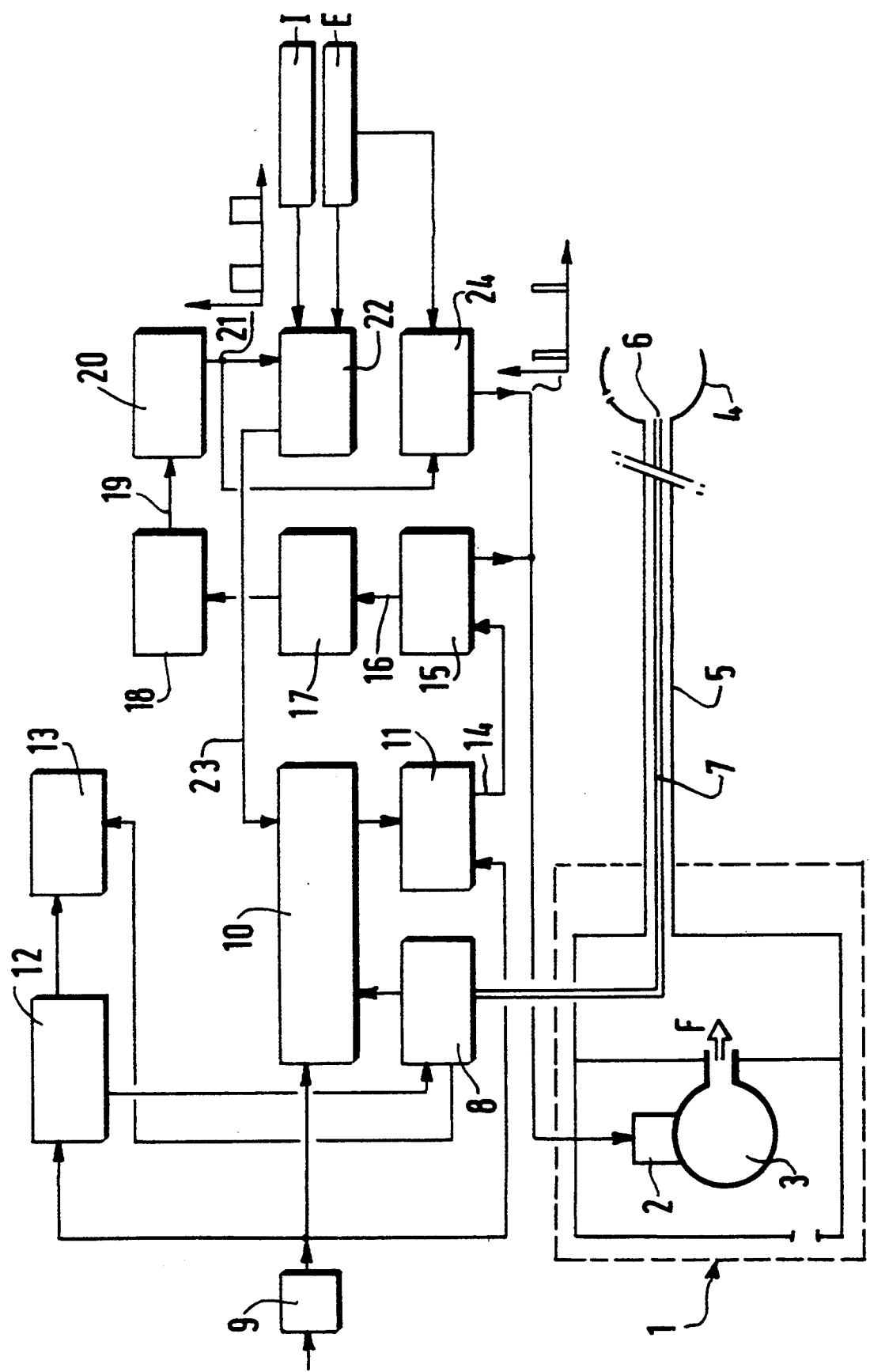

5,443,061

APPARATUS FOR PROVIDING A BREATHING GAS WITH AN OVERPRESSURE AND PROCESS OF CONTROLLING SUCH APPARATUS INSTALLATION

BACKGROUND OF INVENTION (a) Field of the Invention

The present invention concerns a process for controlling an apparatus for providing an overpressure in a breathing gas including a low inertia turbine and means for controlling the turbine by providing a control signal to the turbine as a function of an overpressure of predetermined value, for example for breathing assistance in persons suffering from breathing disorders, in particular during their sleep.

(b) Description of Prior Art

A control apparatus and a process of the type mentioned above are described in French document FR-A-2 663 547, assigned to the assignee of the present invention and incorporated herein by reference. In the known apparatus, the use of a low inertia turbine, whose control flow may be adjusted in real time as a function of the pressure provided thereby and which is directly measured in the mask of the user, assures the user an inhaling pressure which is required for his breathing comfort.

SUMMARY OF INVENTION

It is an object of the present invention to provide a process whereby, with simple and reliable means, at low manufacturing cost, the breathing comfort of the user is improved by the application of a slight increase of overpressure during the inhaling phase of the user.

To do this, according to the invention, recurring variations in the operation of the turbine are detected and in response thereto the predetermined value of the overpressure is modified, thereby to modulate the overpressure provided by the turbine.

More specifically, variations in the operation of the turbine are detected by processing the control signal supplied to the turbine and sequentially providing to the turbine control means two different predetermined values, for example one for the inhaling pressure (I) and one for the exhaling pressure (E) which are set by the operator.

It is another object of the present invention to provide apparatus for providing a breathing gas with an overpressure, comprising a low inertia turbine and means for controlling the turbine by providing to the turbine a control signal that is a function of a pressure of predetermined value to obtain a given delivered overpressure, wherein recurring variations in the operation of the turbine are used to temporarily modify the predetermined pressure value and thereby modulate the overpressure provided by the turbine.

BRIEF DESCRIPTION OF DRAWINGS

Other characteristics and advantages of the present invention will appear from the description which follows of an embodiment, given by way of illustration but without limitation, with reference to the annexed drawing, in which:

the single FIGURE is a schematic representation of an apparatus for providing a breathing gas with an overpressure, according the invention.

DESCRIPTION OF PREFERRED EMBODIMENTS

The mechanical elements of the apparatus described in French patent document FR-A-2 663 547 mentioned above are noted at the bottom of the single FIGURE, namely, a sound proof casing 1, housing a motor unit 2/turbine 3 providing a flow of breathing gas F with a slight overpressure, between 4 and 20 hPa, to a user mask 4 via a breathing gas duct 5, the mask 4 including a pressure intake 6 communicating, via tubular duct 7, with a piezoelectric pressure sensor 8. The apparatus comprises a control and display electronic subassembly, which is supplied with continuous current at 15 V, 2.5 A by means of a power supply 9, the subassembly comprising an electronic central control unit 10 and a power stage 11 connected to motor 2 of the turbine 3 for supplying a driving current thereto. A second power supply 12 supplies a reduced voltage to the pressure sensor 8 and to a supply 13 display stage having electroluminescent diodes for displaying the pressure supplied to the user.

According to the invention, the outlet 14 of the power stage 11, is connected to a detector stage 15 having, for example a low resistance of the order of 0.05 ohm, which detects the motor drive current to produce a signal 16 representative of the start of an inhaling phase or the start of an exhaling phase of the user. The operation of the turbine is controlled by control unit 10 as a function in part of variations of the pressure in the mask 4 detected by sensor 8. The signal 16 is filtered in a low-pass filter 17 and supplied to a differentiator stage 18 which produces at its outlet a signal 19 which is representative of changes or variations in the operation of motor 2 and, thus, of turbine 3. Signal 19 is sent to a shaping circuit 20 which produces an output signal 21 having two conditions 0 and 1.

The apparatus according to the invention additionally comprises a first adjustable stage for setting an inhaling pressure I and a second adjustable stage for setting an exhaling pressure E both pressure settings being supplied as electrical signals to a selector stage 22 which, in turn, couples from its outlet 23 to control unit 10 either of the predetermined values I, E as a function of the conditions 0 and 1 of signal 21.

As indicated above, this arrangement enables the control unit to modify the predetermined value of the control of the overpressure supplied to the user as a function of the breathing cycle of the latter. When the start of an inhaling phase is the control threshold of the overpressure produced by the turbine is brought to a first elevated value (I), which is increased above an initial valve by many centimeters of water, thereby facilitating the introduction of breathing air into the lungs of the user. Then, when the start of an exhaling phase is detected by detector 15, the control threshold of the overpressure is brought back to the initial value (E), thus enabling easier exhaling due to a lowering of the pressure to which the lungs of the user are exposed.

With the arrangement which has just been described, the response of the turbine, because of its low inertia, is quite satisfactory for producing an increase in pressure at the start of the inhaling phase but may still cause a slight exhaling difficulty during a change towards the low pressure threshold (E), at the end of the inhaling cycle. According to an aspect of the invention, in order to improve the operation of the turbine during this transitory phase, there is provided a stage 24 which receives the signal 21 from the shaping module 20 and the signal provided by the second adjustable stage (i.e. the stage the exhaling pressure E) to shunt motor 2 and thereby temporarily slow down the turbine and thus bring it back very rapidly to its operation corresponding to the supplying of the proper overpressure for an exhaling phase of the user. More specifically, stage 24 temporarily by-passes or shunts, the motor 2 of turbine 3, the duration of this shunting being dependent on the value of the exhaling pressure E set by adjustable stage and on the frequency of the inhaling/exhaling cycle of the user.

Although the present invention has been described with reference to a specific embodiment, it is not limited thereby but, on the contrary, it is capable of modifications and variants which will be obvious to one skilled in the art.

We claim:

1. A process of monitoring a respiratory apparatus including an electrically driven low inertia turbine exhibiting operating modes to supply gas to a patient's airways at a determined overpressure in response to a presettable control signal applied thereto, comprising the steps of driving the turbine with a drive current supplied thereto; detecting variations in the drive current supplied to the turbine, thereby to detect variations in the operating mode of the turbine; and correspondingly modifying the control signal in response to said detected variations to modulate the overpressure supplied by the turbine.

2. The process of claim 1, wherein the control signal is processed by filtering and differentiating the control signal, and shaping the filtered differentiated control signal to generate a signal having successive first and second levels.

3. The process of claim 2, further comprising the steps of detecting a transition between said first and second levels, and modifying the control signal in response to said detected transition.

4. The process of claim 3, further comprising the step of slowing down the turbine as a result of said detected transition between the second and first levels of the shaped control signal.

5. The process of claim 4, wherein the slowing down of the turbine is achieved electrically.

6. The process of claim 5, wherein said turbine is driven by an electric motor, and the turbine is slowed down electrically by shunting said electric motor.

7. Apparatus for providing to a patient's airways a determined overpressure, comprising:
a low inertia turbine having an outlet connectable to the patient's airways for supplying gas thereto;
an electric motor exhibiting operating modes for driving the turbine;
at least one electrical power supply for supplying driving current to the motor;
a source of a pressure level setting signal;
control means connected to the motor for monitoring the driving current supplied thereto and thereby monitoring the overpressure supplied by the turbine in response to said pressure level setting signal;
detecting means for detecting variations in the driving current monitored by said control means and thereby detecting variations in the operating mode of the motor and for generating a variation signal; and
means responsive to the variation signal to modify the pressure level setting signal.

8. The apparatus of claim 7, further comprising means coupled to the motor and responsive to the variation signal for slowing down the operation of said motor.

9. The apparatus of claim 8, wherein the means for slowing down the operation of said motor includes a shunt circuit for shunting the motor.

* * * * *